United States Patent [19]

Balasubramanyan et al.

[11] 4,073,923
[45] Feb. 14, 1978

[54] FUNGICIDALLY EFFECTIVE IMIDAZOLES AND USE THEREOF AGAINST FUNGAL PESTS

[75] Inventors: Sugavanam Balasubramanyan, Wokingham; Margaret Claire Shephard, Maidenhead; Patrick Jelf Crowley, Crowthorne, all of England

[73] Assignee: Imperial Chemical Industries Limited, London, England

[21] Appl. No.: 718,206

[22] Filed: Aug. 26, 1976

[30] Foreign Application Priority Data

Sept. 10, 1975 United Kingdom ............... 37244/75

[51] Int. Cl.$^2$ ..................... C07D 233/60; A01N 9/22
[52] U.S. Cl. ............................. 424/273 R; 548/336; 548/341
[58] Field of Search ...................... 260/309; 424/273; 548/336, 341

[56] References Cited

FOREIGN PATENT DOCUMENTS 7,799M 3/1970 France ................................. 260/309

OTHER PUBLICATIONS

City of Hope Medical Center, Chem. Abst. 1972, vol. 76, No. 149226e.
Sunjic et al., Chem. Abst., 1969, vol. 71, No. 90645g.
Chemical Abstracts, Eighth Collective Index for Volumes 66–75, 1967–1971, Subjects Glucope-Indena, p. 15582S, first column, line 6 after imidazole-1-acetic acid ("as preservative for food, 67:89835e").
Miyazawa et al., Chem. Abst., 1967, vol. 67, No. 89835e.
Cook Chem. Abst., 1955, vol. 49, columns 3165–3167.

*Primary Examiner*—Natalie Trousof
*Attorney, Agent, or Firm*—Cushman, Darby & Cushman

[57] ABSTRACT

Fungicidal compounds of the formula:

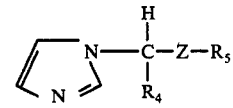

wherein $R_4$ is ethyl or propyl, $R_5$ is hydroxy, $C_{1-14}$ alkoxy, phenylamino, benzyloxy or benzyloxy substituted with halogen and Z is C=O, or a fungicidal salt of said compound.

9 Claims, No Drawings

FUNGICIDALLY EFFECTIVE IMIDAZOLES AND USE THEREOF AGAINST FUNGAL PESTS

This invention relates to heterocyclic compounds which are imidazole to compositions containing them and to methods of combating pests (particularly fungal pests) using them.

The compounds have the general formula (I):

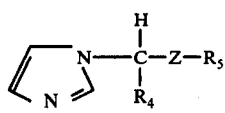

wherein $R_4$ is $C_{1-3}$ alkyl, $R_5$ is hydroxy, $C_{1-14}$ alkoxy, or phenylamino or benzyloxy optionally ring substituted with for example halogen, and Z is C=O or a derivative of said C=O, or the salts of such compounds.

The compounds can contain chiral centre(s). Normally the compounds are prepared in the form of racemic mixtures. However these and other mixtures can be separated into the individual isomers by methods known in the art.

The halogen can be fluorine, chlorine, bromine or iodine.

The phenyl or benzyl group can be substituted by halogen, alkyl, nitro, trifluoromethyl, cyano, alkoxy or alkylenedioxy (e.g. methylenedioxy).

Suitable C=O derivatives are ketals, hydrazones, semicarbazones, imines and oximes.

Examples of suitable $R_4$ groups are methyl, ethyl and propyl (n- or i-propyl).

Suitable $R_5$ groups are methoxy, ethoxy, propoxy (e.g. i-propoxy), butoxy (e.g. n- or t-butoxy), allyloxy, $-OC(CH_3)_2C_2H_5$, $-OCH_2C(CH_3)_3$, $O(CH_2)_2C(CH_3)_3$, n-dodecyloxy, benzyloxy, p-chlorobenzyloxy, phenylamino, o- or p-chlorophenylamino, p-tolylamino, m-chloro-p-tolylamino, p-nitrophenylamino, m-chloro-p-nitrophenylamino, or m-trifluoromethylphenylamino.

The salts of the compounds can be salts of organic or inorganic acids e.g. hydrochloric, sulphuric, acetic or oxalic acid, or, when $R_5$ is hydroxy, salts with alkali metals, for example lithium, sodium or potassium, alkaline earth metals, for example calcium and magnesium, ammonia and primary, secondary or tertiary amines, for example mono-, di- or tri-($C_{1-6}$ aliphatic) amines.

Examples of suitable imidazole compounds wherein Z is C=O are shown in Table I.

TABLE I

| Compound No | $R_4$ | $R_5$ | Melting (Or Boiling) Point ° C |
|---|---|---|---|
| 1 | i-Pr | $-OC_2H_5$ | (94° /0.1 mm) |
| 2 | i-Pr | $-OCH(CH_3)_2$ | (100–5° /0.1 mm) |
| 3 | i-Pr | $-OCH_2CH_2CH_2CH_3$ | (110–15° /0.05 mm) |
| 4 | i-Pr | $-OCH_2CH_2CH_3$ | (125–8° /0.05 mm) |
| 5 | i-Pr | $-NHC_6H_5$ | 182–4° |
| 6 | i-Pr | $-OC(CH_3)_3$ | (100–2° /0.1 mm) |
| 7 | i-Pr | $-OCH_2C(CH_3)_3$ | (110° /0.1 mm) |
| 8 | i-Pr | $-O-n-C_{12}H_{25}$ | not distilled (liquid) |
| 9 | i-Pr | $-OCH_2CH_2CH(CH_3)_2$ | (110° /0.03 mm) |
| 10 | i-Pr | $-OCH_2CH(CH_3)_2$ | (110° /0.01 mm) |
| 11 | i-Pr | 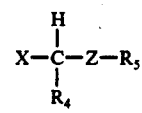 | not distilled (liquid) |
| 12 | i-Pr | $-OCH(C_2H_5)_2$ | (110° /0.005 mm) |
| 13 | i-Pr | $-OC(CH_3)_2C_2H_5$ | (105–10° /0.02 mm) |
| 14 | i-Pr | $-OCH_2CH(CH_3)CH_2CH_3$ | (140–5° /0.02 mm) |
| 15 | i-Pr | $-O^- K^+$ | 104–5° |

The compounds may be made by reacting imidazole or a salt thereof with the appropriate activated halo compound (for example an α-haloketone, α-haloacid, α-haloester, α-haloamide or substituted alkyl halide) using methods set out in the literature. Thus imidazole or a salt thereof, can be reacted with a compound of general formula (II):

$$X-\underset{R_4}{\underset{|}{\overset{H}{\overset{|}{C}}}}-Z-R_5$$

wherein X is halogen, preferably bromine or chlorine, and Z, $R_4$ and $R_5$ are as defined above.

Alternatively, the compounds wherein $R_4$ is other than hydrogen can be made by hydrocarbylating (e.g. with an appropriately substituted alkylating or aralkylating agent) a compound of general formula (III):

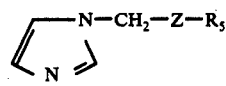

wherein $R_5$ and Z are as defined above, or a salt thereof, suitably in the presence of a base in a hydroxylic or non-hydroxylic solvent using methods set out in the literature.

These processes may in some cases be carried out by heating the reactants together in the absence of a solvent or diluent, but preferably a solvent is present. Suitable solvents are non-hydroxylic solvents such as acetonitrile (which is preferred), dimethylformamide, dimethyl sulphoxide, sulpholane and tetrahydrofuran. Hydroxylated solvents, for example methanol and ethanol, may be used in certain circumstances when the presence of the hydroxyl group does not interfere with the progress of the reaction. The processes may also be carried out in the presence of a base, but preferably excess imidazole is present to remove liberated HX from the reaction. Other suitable bases are sodium hydride (although not when a hydroxylated solvent or diluent is used), alkali metal carbonates (such as potassium carbonate) and alkali metal hydroxides (such as potassium hydroxide). The reaction temperature depends upon the choice of reactants, solvent and base, but generally the reaction mixture is refluxed.

The processes generally involve dissolving the reactants in a solvent and, after allowing reaction to occur, isolating the product by removal of the reactant solvent in vacuo.

The unreacted imidazole is removed by extraction of the product with a suitable solvent and the extract is washed with water. A crystallisation or other purification procedure may then be carried out if desired.

The activated halo compounds may be made by any of the methods set out in the literature.

The compounds wherein Z is C=O may be converted in known manner to the C=O derivatives.

The compounds are active fungicides, particularly against the following diseases:

*Piricularia oryzae* on rice

*Puccinia recondita* and other rusts on wheat and rusts on other hosts

*Plasmopara viticola* on vines

*Erysiphe graminis* (powdery mildew) on barley and wheat and other powdery mildews on various hosts such as *Sphaerotheca fulginea* on cucumbers, *Podosphaera leucotricha* on apples and *Uncinula necator* on vines

*Botrytis cinerea* (grey mould) on tomatoes, strawberries, vines and other hosts Some of the compounds are active in the form of seed dressings against:

*Fusarium spp., Septoria spp., Tilletia spp.,* and *Pyrenophora spp.* on cereals.

The compounds also have certain anti-bacterial and anti-viral activities.

They may be used as such for anti-fungal purposes but are more conveniently formulated into compositions for such usage.

The invention therefore also provides a fungicidal composition comprising, as an active ingredient, an imidazole compound or salt thereof, and a carrier for the active ingredient.

The invention also provides a method for combating pests, which are fungi, viruses or bacteria, which method comprises treating plants, seeds or trees with an imidazole compound or salt thereof as hereinbefore defined.

The compounds can be used to combat plant pests and treat plants or seeds in a number of ways, for example they can be applied, formulated or unformulated, directly to the foliage of a plant which is infected or likely to become infected, or they can be applied also to bushes and trees, to seeds or to other medium in which plants, bushes or trees are growing or are to be planted, or they can be sprayed on, dusted on or applied as a cream or paste formulation. Application can be to any part of the plant, bush or tree, for example to the foilage, stems, branches or roots, or to soil surrounding the roots.

The term "treating" as used herein refers to all these modes of application and the term "plant" includes seedlings, bushes and trees. Furthermore, the method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable solvents are ethylene dichloride, isopropyl alcohol, propylene glycol, diacetone alcohol, toluene, kerosene, methylnaphthalene, the xylenes and trichloroethylene.

The compositions to be used as sprays may also be in the form of aerosols wherein the formulation is held in a container under pressure in the presence of a propellant, e.g. fluorotrichloromethane or dichlorodifluoromethane.

By including suitable additives, for example additives for improving the distribution, adhesive power and resistance to rain on treated surfaces, the different compositions can be better adapted for various utilities.

The compounds can be used as mixtures with fertilisers (e.g. nitrogen — or phosporus — containing fertilisers). Compositions comprising only granules of fertiliser incorporating, for example coated with, the imidazole compound, are preferred. The invention therefore also provides a fertiliser composition comprising the imidazole compound.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-anionic agents.

Suitable cationic agents are quaternary ammonium compounds for example, cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butyl-naphthalene sulphonate, and a mixture of sodium diisopropyl- and triisopropyl-naphthalene sulphonates). Suitable non-ionic agents are the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportions of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10-85%, generally 25-60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, as well as stabilising agent(s), for example epoxides (e.g. epichlorhydrin).

The following Examples illustrate the invention; the temperatures are given in degrees Centigrade (° C).

EXAMPLE 1

Ethyl 2-(1-imidazolyl)-3-methylbutyrate.

(Compound 1)

Ethyl 2-bromo-2-isopropyl acetate (5 g), imidazole (4.2 g) and acetonitrile were refluxed for 72 hours. The solvent was removed in vacuo and the residue slurried with diethyl ether and poured into water. The ethereal layer was separated off and dried (magnesium sulphate). The solvent was removed in vacuo to give an oil which on distillation gave the title compound, b.p. 55°-60°/0.1 mm.

EXAMPLE 2

The compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots. Vermiculite was used to cover the seed in the soil tests.

The compounds were formulated either by bead-milling with aqueous Dispersol T or as a solution in acetone/ethanol ethanol which was diluted to the required concentration immediately before use. For the foliage diseases, 100 ppm a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil and foilage one or two days before the plant was inoculated with the diseases. An exception was the test on *Erysiphe graminis*, in which the plants were inoculated 24 hours before treatment. After inoculation, the plants were put into an appropriate environment to allow infection to take place and then incubated until the disease was ready for assessment. The period between inoculation and assessment varied from 3 to 10 days according to the disease and environment.

The disease control was recorded by the following grading:

4 = No desease
3 = 0-5%
2 = 6-25%
1 = 26-60%
0 = >60%

The results are shown in Table II.

TABLE II

| COMPOUND NO | DISEASE (DAYS BETWEEN INFECTION AND ASSESSMENT) | | | | | |
|---|---|---|---|---|---|---|
| | *Puccinia recondita* in wheat (10 days) | *Phytophthora infestans* in tomato (3 days) | *Plasmopara viticola* in vines (7 days) | *Piricularia oryzae* in rice (7 days) | *Botrytis cinerea* in tomatoes (3 days) | *Erysiphe graminis* in barley (7 days) |
| 1 | 2 | 0 | — | 2 | 2 | 4 |
| 2 | 3 | 0 | — | 2 | 0 | 4 |
| 3 | 3 | 1 | — | 0 | 0 | 4 |
| 4 | 4 | 2 | 1 | 3 | 2 | 4 |
| 5 | 4 | 0 | — | 0 | 0 | 4 |
| 6 | 4 | 0 | 0 | 0 | 0 | 3 |
| 7 | 4 | 0 | 0 | 0 | 0 | 3 |
| 8 | 1 | 1 | 0 | 2 | 0 | 3 |
| 9 | 3 | 0 | 0 | 3 | 2 | 4 |
| 10 | — | | 0 | 0 | 3 | 4 |
| 11 | | | | | | |
| 11 | | | | | | |
| 12 | | | | | | |
| 13 | | | | | | |
| 14 | | | | | | |
| 15 | | | | | | |

We claim:

1. A compound of the formula (I):

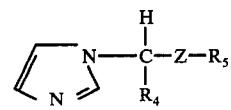

wherein $R_4$ is ethyl or propyl, $R_5$ is hydroxy, $C_{1-14}$ alkoxy, phenylamino, benzyloxy or benzyloxy substituted with halogen and Z is C=O, or a fungicidal salt of said compound.

2. A compound as claimed in claim 1 wherein $R_4$ is i-propyl and $R_5$ is hydroxy; $C_{1-4}$ alkoxy; phenylamino; unsubstituted benzyloxy or benzyloxy substituted with halogen.

3. A compound according to claim 1 wherein $R_4$ is i-propyl and $R_5$ has one of the following values:

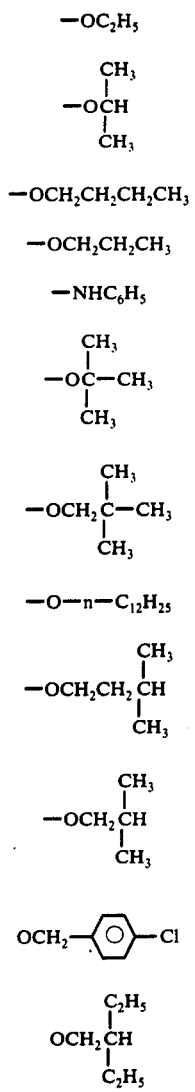

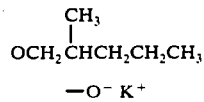

—O⁻ K⁺

4. A compound according to claim 3 wherein $R_4$ is i-propyl and $R_5$ is —OC$_2$H$_5$.

5. A fungicidal composition consisting essentially of as active ingredient, a fungicidally effective amount of a compound or salt as claimed in claim 1, and a carrier for the active ingredient.

6. A fungicidal composition consisting essentially of, as active ingredient, a fungicidally effective amount of a compound or salt as claimed in claim 2 and a carrier for the active ingredient.

7. A method of combating fungal diseases in a plant, said method consisting essentially of the step of applying to the plant, or to the locus of the plant, a fungicidally effective amount of a compound of the formula:

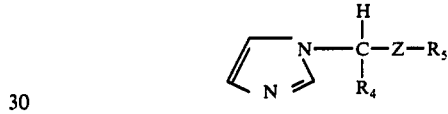

wherein $R_4$ is $C_{1-3}$ alkyl, $R_5$ is hydroxy, $C_{1-14}$ alkoxy, phenylamino, benzyloxy or benzyloxy substituted with halogen and Z is C=O, or a fungicidal salts of said compound.

8. A method of combating fungal diseases in a plant, said method consisting essentially of the step of applying to the plant, or to the locus of the plant, a fungicidally effective amount of a compound or salt as claimed in claim 2.

9. A method of combating fungal diseases in a plant, said method consisting essentially of the step of applying to the plant, or to the locus of the plant, a fungicidally effective amount of a compound or salt as claimed in claim 3.

* * * * *